(12) United States Patent
Wang

(10) Patent No.: US 8,755,882 B2
(45) Date of Patent: Jun. 17, 2014

(54) CLOSED LOOP OPTIMIZATION OF A-V AND V-V TIMING

(75) Inventor: Li Wang, Shanghai (CN)

(73) Assignee: Medtronic, Inc., Minneapolis, MN (US)

( * ) Notice: Subject to any disclaimer, the term of this patent is extended or adjusted under 35 U.S.C. 154(b) by 816 days.

(21) Appl. No.: 12/962,245

(22) Filed: Dec. 7, 2010

(65) Prior Publication Data

US 2011/0172728 A1    Jul. 14, 2011

Related U.S. Application Data

(63) Continuation of application No. 11/323,314, filed on Dec. 30, 2005, now Pat. No. 7,848,807.

(51) Int. Cl.
*A61N 1/362* (2006.01)
*A61N 1/375* (2006.01)
*A61B 5/0452* (2006.01)

(52) U.S. Cl.
CPC ............ *A61N 1/3756* (2013.01); *A61B 5/0452* (2013.01); *A61N 1/362* (2013.01)
USPC .................... 607/9; 607/11; 607/17; 607/115; 607/116; 607/119

(58) Field of Classification Search
CPC ... A61N 1/3622; A61N 1/368; A61N 1/3682; A61N 1/365; A61N 1/37; A61N 1/3702; A61N 1/362; A61N 1/00; A61N 1/05; A61N 1/3756; A61B 5/0452; A61B 5/0468; A61B 5/0408

USPC ............ 607/1–2, 9, 11, 17, 25, 115–116, 119
See application file for complete search history.

(56) References Cited

U.S. PATENT DOCUMENTS

| | | |
|---|---|---|
| 4,310,000 A | 1/1982 | Lindemans |
| 5,312,441 A | 5/1994 | Mader |
| 5,331,966 A | 7/1994 | Bennett et al. |
| 5,564,434 A | 10/1996 | Halperin |
| 5,755,739 A | 5/1998 | Sun et al. |
| 6,421,564 B1 | 7/2002 | Yerich |
| 6,694,189 B2 | 2/2004 | Begemann |
| 6,760,622 B2 | 7/2004 | Helland |
| 2003/0130702 A1 | 7/2003 | Kramer |
| 2004/0236379 A1 | 11/2004 | Bardy et al. |
| 2005/0137634 A1 | 6/2005 | Hall |
| 2005/0149137 A1 | 7/2005 | Chinchoy et al. |

*Primary Examiner* — Deborah Malamud
(74) *Attorney, Agent, or Firm* — Reed A. Duthler

(57) ABSTRACT

Embodiments of close loop optimization of atrio-ventricular (A-V) delay interval and/or inter-ventricular (V-V) timing are disclosed. An implantable medical device includes a housing that supports a processing means adapted for implantation in a patient. There can be two or more electrodes electrically coupled to the processing means where the two or more electrodes can be used for sensing a patient's cardiac signals, which include a far-field EGM. The processing means can determine a width of a P-wave from the sensed far-field EGM. Also included can be a means for delivering an adapted cardiac pacing therapy based upon the width of the P-wave, including revised A-V delay and/or V-V temporal intervals.

24 Claims, 6 Drawing Sheets

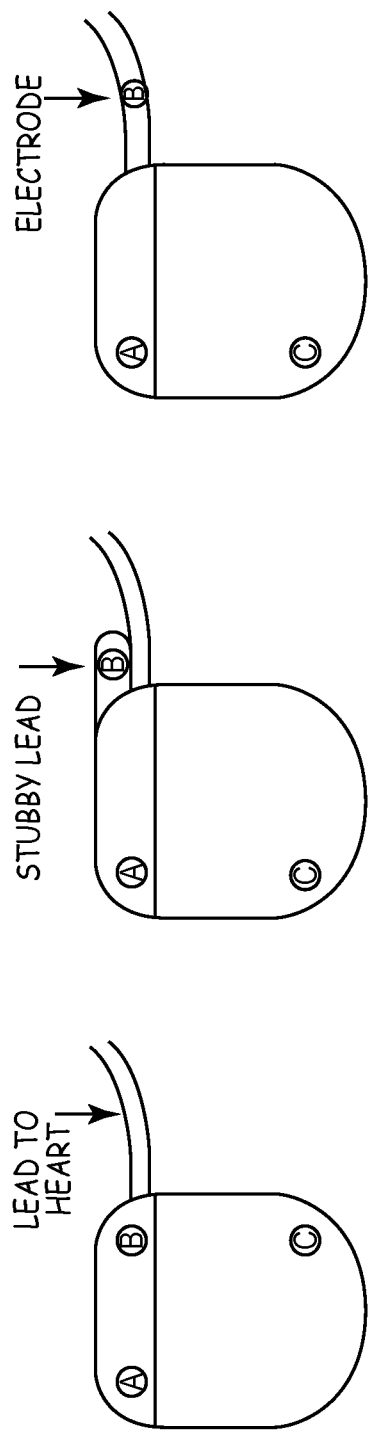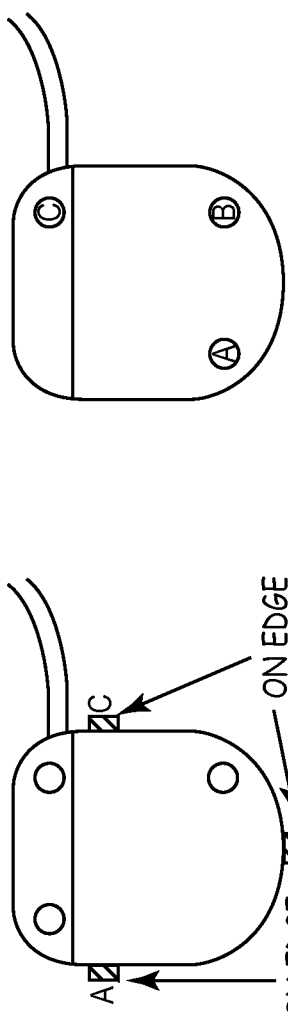

CLOSED LOOP OPTIMIZATION OF A-V AND V-V TIMING

RELATED APPLICATION

This application is a continuation of U.S. patent application Ser. No. 11/323,314, filed Dec. 30, 2005 entitled "CLOSED LOOP OPTIMIZATION OF A-V AND V-V TIMING", herein incorporated by reference in its entirety.

BACKGROUND

Many embodiments in the present disclosure relate to implantable cardiac pulse generators (IPGs) generally, and more particularly to implantable cardioverters defibrillators (ICDs) and triple-chamber pacing devices configured to deliver cardiac resynchronization therapy (CRT).

Cardiac conduction defects and various co-morbidities of heart failure can confound the natural cardiac depolarization sequence so that upper and lower chambers fail to electrically conduct and mechanically contract during normal sinus rhythm (NSR) and/or without ventricular synchrony. In certain heart failure patients, the heart may become dilated, and the conduction and depolarization sequences of the heart chambers may, for example, exhibit inter- and/or intra-atrial conduction defects (IACD), left bundle branch block (LBBB), right bundle branch block (RBBB), and inter-ventricular conduction defects (IVCD) and the like. In patients suffering from each or a combination of such conduction defects, a lack of synchrony and/or complementary blood flow among the chambers can diminish cardiac output and impair perfusion of the organs of tissues of the patient. In addition, spontaneous depolarizations originating within the right atrium, left atrium (RA,LA), the right ventricle (RV), and/or the left ventricle (LV) can arise from diverse locations (e.g., at one or more ectopic foci) thus disturbing the natural activation sequence. Further, significant conduction disturbances between the RA and LA can result in atrial flutter or fibrillation (e.g., which can significantly impair LV filling due to the arrthymia within the LA).

It has been proposed that various conduction disturbances involving both bradycardia and tachycardia conditions could be overcome by applying pacing pulses at multiple electrode sites positioned in or about a single or multiple chambers of a heart in synchrony with a depolarization that is sensed at one of multiple electrode sites. It is believed that cardiac output can be significantly improved when left and right chamber synchrony is restored, particularly in patients suffering from dilated cardiomyopathy and heart failure.

For patients with dual chamber or triple chamber implantable devices appropriate timing between the RA and RV and the LA and LV is beneficial to achieve optimal hemodynamics. One consideration for selecting the appropriate timing is the time relationship between right and left atrial contraction. In current implantable systems, RA contraction can be determined from the RA electrical depolarization sensed from one or more electrodes coupled to a lead disposed in communication with the RA. In these systems, there is no good way to determine the electrical depolarization and mechanical contraction timing of the LA. This is because the bipolar RA electrogram (EGM) mostly represents the localized electrical activities (e.g., near field) in the RA and not the LA. The unipolar RA EGM from the RA tip also suffers from the similar limitation as the tip signal is dominated by the local myocardium around the tip electrode.

In current practice, clinicians have used Doppler echocardiography to guide A-V and/or V-V optimization in patients with CRT. They are typically done a month or so after implant. Sometimes, clinicians would only selectively perform so-called echo-guided optimization in non-responder patients (i.e., patients that fail to improve hemodynamics in response to CRT delivery) due to increased number of device implants as well as difficulties in scheduling visits to qualified clinicians such as an electrophysiologist or an echo technician. However, it is unknown whether the A-V delay interval or inter-ventricular (V-V) interval, if any, selected during an echo-guided optimization performed when the patient is supine and resting are the same as when the patient is ambulatory and active. Similarly, as the patient's disease state evolves, for example, due to an acute heart failure decompensation event or because of deleterious remodeling that occurs in the progression of heart failure or otherwise during the course of heart failure treatment and therapy, it is foreseeable that the A-V and/or V-V timing would change as well and thus benefit from a closed loop method and apparatus for adapting to same.

DRAWINGS

FIGS. 5A-5E are schematic illustrations of possible three electrode positions on the case and/or lead of an implantable medical device for practicing the concepts of the present invention;

DESCRIPTION OF VARIOUS EMBODIMENTS

Figure 1:
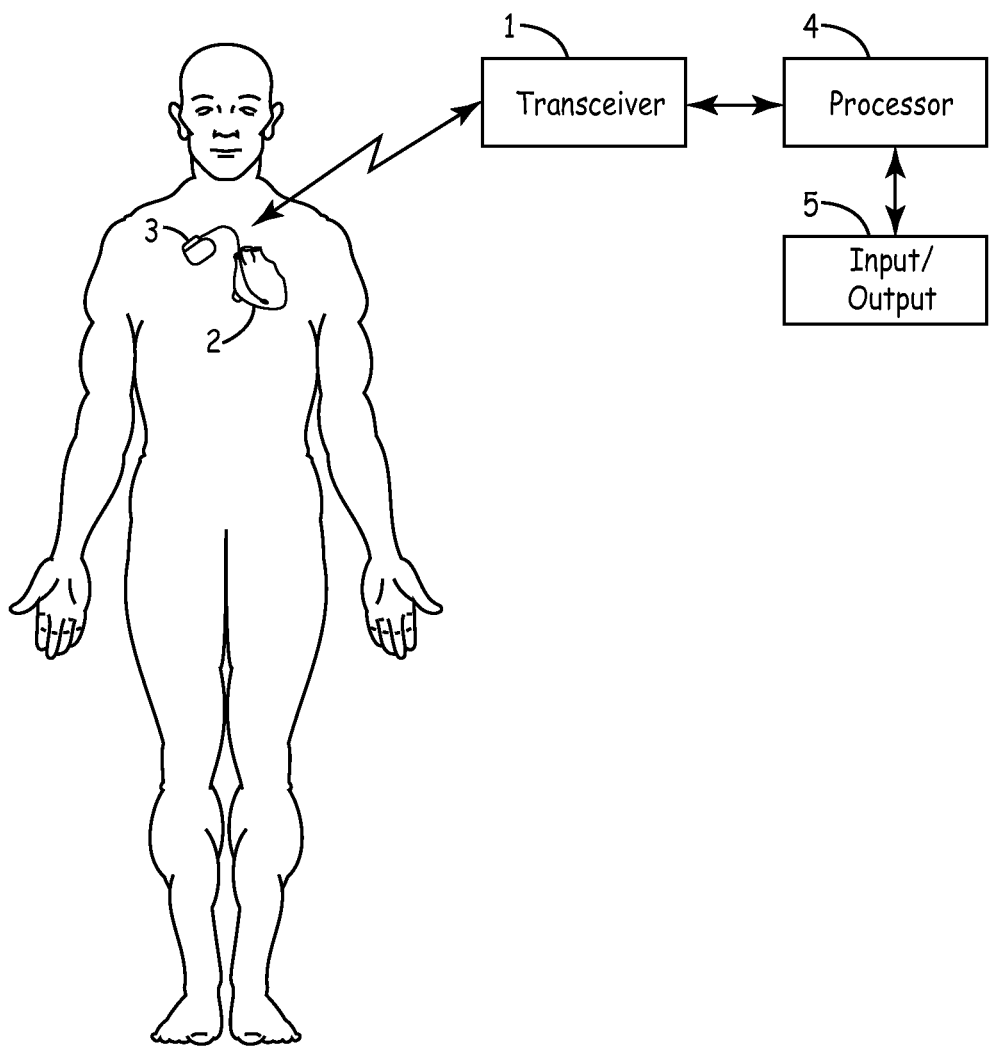
FIG. 1 shows an implanted device such as a pacemaker in an embodiment of the present invention.

The following discussion is presented to enable a person skilled in the art to make and use embodiments of the invention. Various modifications to the illustrated embodiments will be readily apparent to those skilled in the art, and the generic principles herein may be applied to other embodiments and applications without departing from embodiments of the invention. Thus, embodiments of the invention are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of embodiments of the invention. Skilled artisans will recognize the examples provided herein have many useful alternatives and fall within the scope of embodiments of the invention. The following introductory material is intended to familiarize the reader with the general nature and some of the features of embodiments of the invention.

Referring now to FIG. 1, a diagram is shown illustrating the environment of the apparatus and method of certain embodiments of this invention. The invention may be used with an implantable device such as a pacemaker 3, illustrated as implanted within a patient. Connected to the pacemaker is a lead 2, which extends into the patient heart, and has one or more electrodes at the distal end thereof that deliver stimulus pulses and also sense intracardiac or epicardial signals. As is well known in the pacemaker art, the sense signals can be received by the pacemaker, digitized and stored in memory, for later transmission to an external device; alternately, they can be downloaded directly to an external programmer device. Likewise, one or more sensors located on the lead or in the pacemaker can produce the signals that are to be digitized and stored. As shown, the transceiver 1 may be a conventional programmer as used in the pacemaker art. The programmer, when it has received data from the pacemaker, can transfer it to a processor 4, which in turn can output data to input/output device 5, all in a well-known manner.

Figure 2:
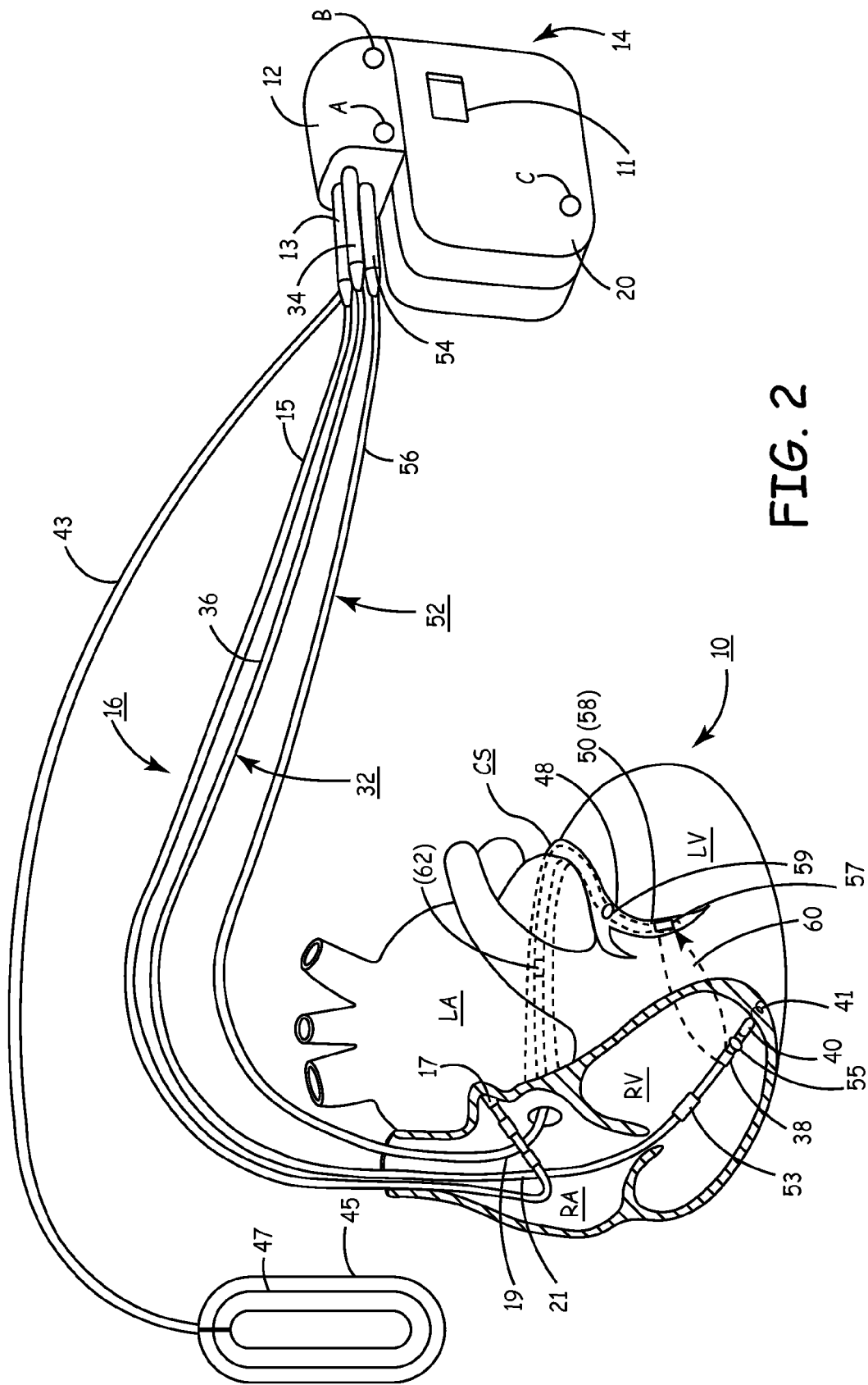
FIG. 2 is a schematic diagram depicting a multi-channel, atrial and bi-ventricular, monitoring/pacing implantable medical device (IMD) in which embodiments of the invention are preferably implemented.

FIG. 2 depicts an implanted, multi-channel cardiac pacemaker, ICD, IPG (implantable pulse generator) or other IMD of the above noted types for restoring A-V synchronous contractions of the atrial and ventricular chambers and simultaneous or sequential pacing of the right and left ventricles. The pacemaker IPG 14 is implanted subcutaneously in a patient's body. Up to three endocardial leads 16, 32, and 52 connect the IPG 14 with the RA, the RV and the LV, respectively. Each lead includes at least one electrical conductor and pace/sense electrode, and a remote indifferent can electrode 20 is formed as part of the outer surface of the housing of the IPG 14. As described further below, the pace/sense electrodes and the remote indifferent can electrode 20 (IND_CAN electrode) can be selectively employed to provide a number of unipolar and bipolar pace/sense electrode combinations for pacing and sensing functions. The depicted positions in or about the right and left heart chambers are also merely exemplary. Moreover other leads and pace/sense electrodes may be used instead of the depicted leads and pace/sense electrodes that are adapted to be placed at electrode sites on or in or relative to the RA, LA, RV and LV.

The depicted bipolar endocardial RA lead 16 is passed through a vein into the RA chamber of the heart 10, and the distal end of the RA lead 16 is attached to the RA wall by an attachment mechanism 17. The bipolar endocardial RA lead 16 is formed with an in-line connector 13 fitting into a bipolar bore of IPG connector block 12 that is coupled to a pair of electrically insulated conductors within lead body 15 and connected with distal tip RA pace/sense electrode 19 and proximal ring RA pace/sense electrode 21. Delivery of atrial pace pulses and sensing of atrial sense events is effected between the distal tip RA pace/sense electrode 19 and proximal ring RA pace/sense electrode 21, wherein the proximal ring RA pace/sense electrode 21 functions as an indifferent electrode (IND_RA). Alternatively, a unipolar endocardial RA lead could be substituted for the depicted bipolar endocardial RA lead 16 and be employed with the IND_CAN electrode 20. Or, one of the distal tip RA pace/sense electrode 19 and proximal ring RA pace/sense electrode 21 can be employed with the IND_CAN electrode 20 for unipolar pacing and/or sensing.

Bipolar, endocardial RV lead 32 is passed through the vein and the RA chamber of the heart 10 and into the RV where its distal ring and tip RV pace/sense electrodes 38 and 40 are fixed in place in the apex by a conventional distal attachment mechanism 41. The RV lead 32 is formed with an in-line connector 34 fitting into a bipolar bore of IPG connector block 12 that is coupled to a pair of electrically insulated conductors within lead body 36 and connected with distal tip RV pace/sense electrode 40 and proximal ring RV pace/sense electrode 38, wherein the proximal ring RV pace/sense electrode 38 functions as an indifferent electrode (IND_RV). Alternatively, a unipolar endocardial RV lead could be substituted for the depicted bipolar endocardial RV lead 32 and be employed with the IND_CAN electrode 20. Or, one of the distal tip RV pace/sense electrode 40 and proximal ring RV pace/sense electrode 38 can be employed with the IND_CAN electrode 20 for unipolar pacing and/or sensing. Also depicted in FIG. 2 is an RV sensor 55 and an LV sensor 59 which may comprise one or more of a variety of sensors as is known in the art. Preferably RV sensor 55 comprises an absolute pressure sensor, but other pressure sensors may be utilized. In addition, RV sensor 55 may comprise an accelerometer, an impedance electrode, a saturated oxygen sensor, a pH sensor, and the like. Of course, such sensors must be rendered biocompatible and reliable for long-term use. In addition, one or more sensors may be disposed in or on the housing 20 of IMD 14 such as sensors A, B, or C depicted in FIG. 2.

Figure 3:
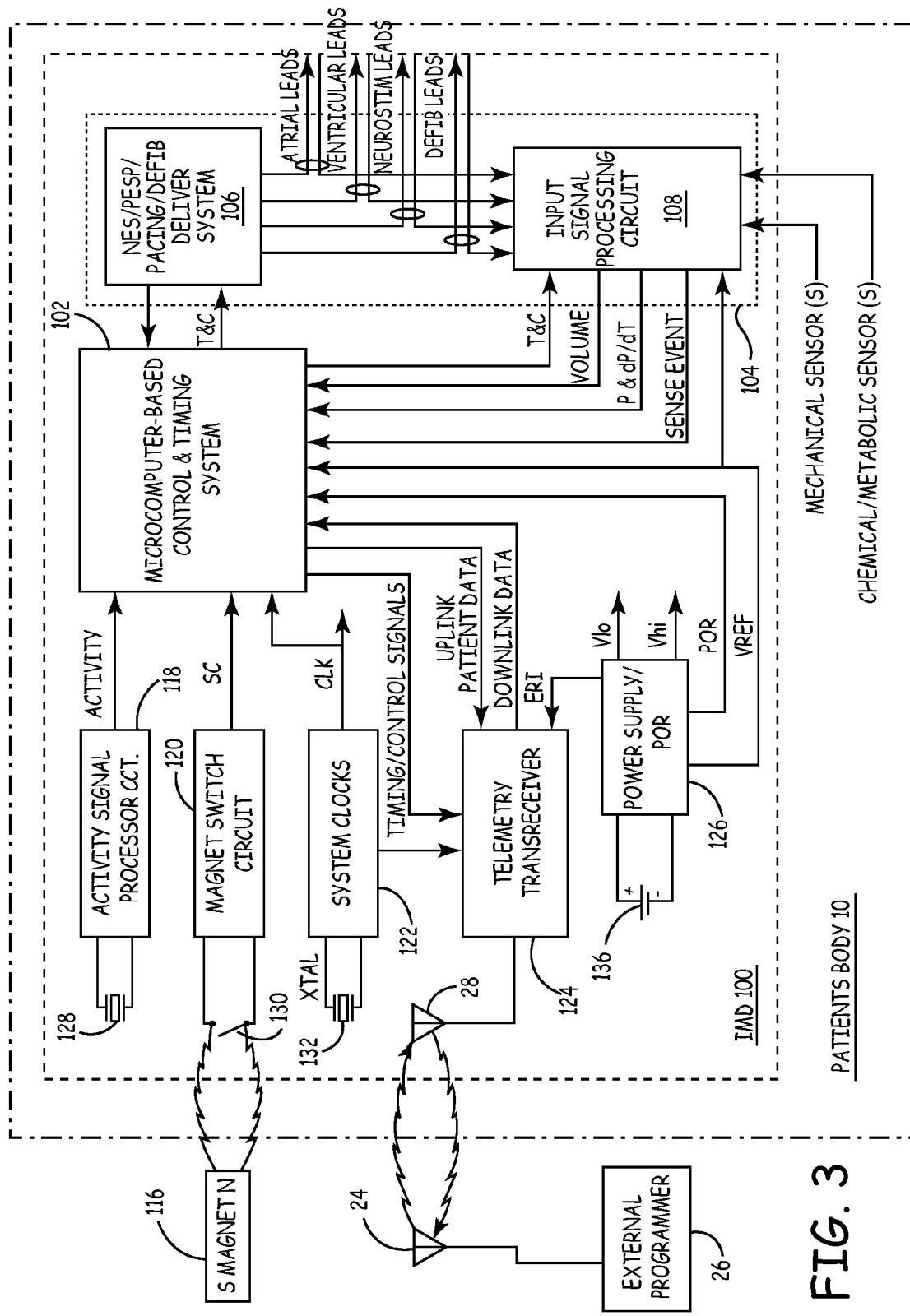
FIG. 3 is a simplified block diagram of one embodiment of IPG circuitry and associated leads employed in the system of FIG. 2 enabling therapy delivery and heart failure state monitoring in one or more heart chambers.

FIG. 3A depicts a system architecture of an exemplary multi-chamber IMD 100 implanted into a patient's body 10 that provides delivery of a therapy and/or physiologic input signal processing. The typical multi-chamber monitor/sensor 100 has a system architecture that is constructed about a microcomputer-based control and timing system 102 that varies in sophistication and complexity depending upon the type and functional features incorporated therein. The functions of microcomputer-based multi-chamber monitor/sensor control and timing system 102 are controlled by firmware and programmed software algorithms stored in RAM and ROM including PROM and EEPROM and are carried out using a CPU, ALU, etc., of a typical microprocessor core architecture. Of course, such firmware and software may be modified in situ (e.g., in vivo) and the operational characteristics may be adapted for a particular situation or patient. A physician or clinician may change one or more parameters that will cause a change in the detection or response of such algorithms. Discrete values may be changed such that a desired software routine is advantageously altered, although sometimes an entirely new set of operating software may be substituted for an existing set of operating software, as is known in the art. The microcomputer-based multi-chamber monitor/sensor control and timing system 102 may also include a watchdog circuit, a DMA controller, a block mover/reader, a CRC calculator, and other specific logic circuitry coupled together by on-chip data bus, address bus, power, clock, and control signal lines in paths or trees in a manner well known in the art. It will also be understood that control and timing of multi-chamber monitor/sensor 100 can be accomplished with dedicated circuit hardware or state machine logic rather than a programmed microcomputer.

The multi-chamber monitor/sensor 100 also typically includes patient interface circuitry 104 for receiving signals from sensors and pace/sense electrodes located at specific sites of the patient's heart chambers and/or delivering stimulation to derive heart failure parameters or a pacing therapy to the heart chambers. The patient interface circuitry 104 therefore comprises a stimulation delivery system 106 optionally including pacing and other stimulation therapies and a physiologic input signal processing circuit 108 for processing the blood pressure and volumetric signals output by sensors. For purposes of illustration of the possible uses of these embodiments of the invention, a set of lead connections are depicted for making electrical connections between the therapy delivery system 106 and the input signal processing circuit 108 and sets of pace/sense electrodes located in operative relation to the RA, LA, RV and LV.

The physiologic input signal processing circuit 108 therefore includes at least one electrical signal amplifier circuit for amplifying, processing and in some cases detecting sense events from characteristics of the electrical sense signal or sensor output signal. The physiologic input signal processing circuit 108 in multi-chamber monitor/sensors providing dual chamber or multi-site or multi-chamber monitoring and/or pacing functions includes a plurality of cardiac signal sense channels for sensing and processing cardiac signals from sense electrodes located in relation to a heart chamber. Each such channel typically includes a sense amplifier circuit for detecting specific cardiac events and an EGM amplifier circuit for providing an EGM signal to the control and timing system 102 for sampling, digitizing and storing or transmitting in an uplink transmission. Atrial and ventricular sense amplifiers include signal processing stages for detecting the occurrence of a P-wave, R-wave, or T-wave respectively and providing an ASENSE, VSENSE or TSENSE event signal to the control and timing system 102. Timing and control system 102 responds in accordance with its particular operating system to deliver or modify a pacing therapy, if appropriate, or to accumulate data for uplink telemetry transmission or to provide a Marker Channel® signal in a variety of ways known in the art. In addition, the input signal processing circuit 108 includes at least one physiologic sensor signal processing channel for sensing and processing a sensor derived signal from a physiologic sensor located in relation to a heart chamber or elsewhere in the body.

Figure 4:
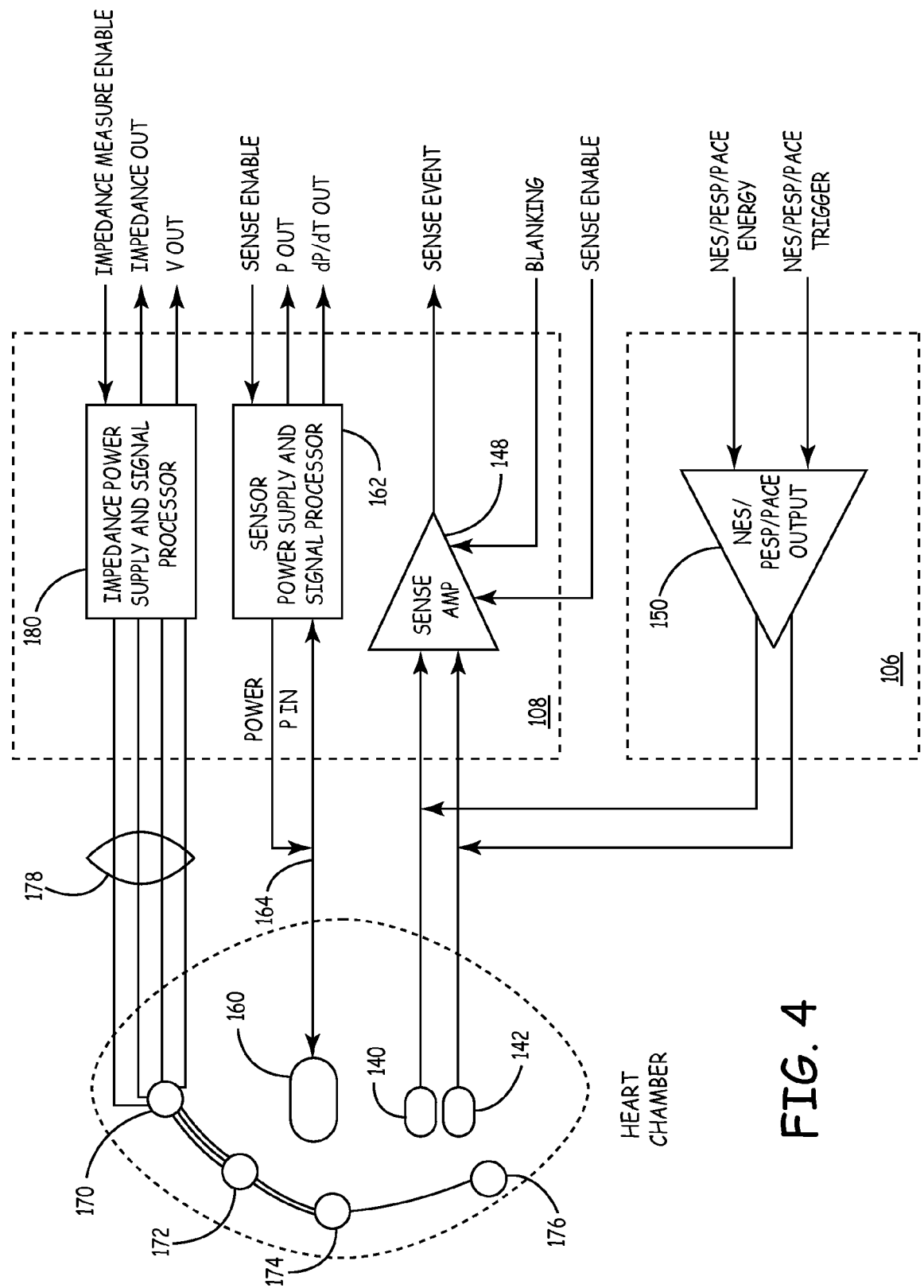
FIG. 4 is a simplified block diagram of a single monitoring and pacing channel for deriving pressure, impedance and cardiac EGM (electrogram) signals employed in monitoring heart failure and optionally pacing the heart and delivering therapy in accordance with the embodiments of the invention.

FIG. 4 schematically illustrates one pacing, sensing, and parameter measuring channel in relation to one heart chamber. A pair of pace/sense electrodes 140, 142, a sensor 160, and a plurality, e.g., four, impedance measuring electrodes 170, 172, 174, 176 are located in operative relation to the heart chamber. The pair of pace/sense electrodes 140, 142 are located in operative relation to the heart chamber and coupled through lead conductors 144 and 146, respectively, to the inputs of a sense amplifier 148 located within the input signal processing circuit 108. The sense amplifier 148 is selectively enabled by the presence of a sense enable signal that is provided by control and timing system 102. The sense amplifier 148 is enabled during prescribed times when pacing is either enabled or not enabled as described below in reference to the measurement of the parameters of heart failure. The blanking signal is provided by control and timing system 102 upon delivery of a pacing pulse or pulse train to disconnect the sense amplifier inputs from the lead conductors 144 and 146 for a short blanking period in a manner well known in the art. When sense amplifier 148 is enabled and is not blanked, it senses the electrical signals of the heart, referred to as the EGM, in the heart chamber. The sense amplifier provides a sense event signal signifying the contraction of the heart chamber commencing a heart cycle based upon characteristics of the EGM, typically the P-wave when the heart chamber is the RA or LA and the R-wave, when the heart chamber is the RV or LV, in a manner well known in the pacing art. The control and timing system responds to non-refractory sense events by restarting an escape interval (EI) timer timing out the EI for the heart chamber, in a manner well known in the pacing art.

The pair of pace/sense electrodes 140, 142 are also coupled through lead conductors 144 and 146, respectively, to the output of a pulse generator 150. The pulse generator 150, within pacing delivery system 106, selectively provides a pacing pulse to electrodes 140, 142 in response to a PACE trigger signal generated at the timing system 102 in a manner well known in the pacing art.

The sensor 160 and/or other physiologic sensor is coupled to a sensor power supply and signal processor 162 within the input signal processing circuit 108 through a set of lead conductors 164 that convey power to the sensor 160 to the sensor power supply and signal processor 162. The sensor power supply and signal processor 162 samples the blood pressure impinging upon a transducer surface of the sensor 160 located within the heart chamber when enabled by a sense enable signal from the control and timing system 102. As an example, absolute pressure P, developed pressure DP and pressure rate of change dP/dt sample values can be developed by sensor power supply and signal processor unit 162 or by the control and timing system 102 for storage and processing as described further below. The sensor 160 and a sensor power supply and signal processor 162 may take the form disclosed in commonly assigned U.S. Pat. No. 5,564,434.

Many embodiments of the present invention are geared towards detecting the width of the P-wave. A helpful aspect of this method is to know the electrical activation of both RA and LA. This allows the stimulation of the right and left ventricle at the appropriate time to allow the full RA and LA contribution of ventricular filling and therefore optimize the hemodynamics of ventricular contraction. This is accomplished by using the far field (not near field) atrial electrograms (EGMs) recorded from the implantable CRT device. This far field EGM provides the P-wave similar to the surface ECG that has electrical activation from both right and left atria. The intrinsic RA and LA activation is different from the paced RA and LA activation. This method also provides the different A-V and V-V timings for paced or sensed P-waves. The use of near field P-wave sensing may potentially be limited in providing P-wave width for the paced P-wave, as the electrode pair for sensing P-wave width is shared with pacing electrode. With the high pacing energy on the electrodes, sensing P-wave becomes very difficult.

Detecting the P-wave width is helpful in diagnosing heart failure patients. If a patient starts to show a widening of the P-wave, then this could be a precursor of heart failure and treatments could be implemented either dynamically or through optimization by a physician programming an implantable device based upon information relayed to the physician from IPG 14. A widening of the P-wave shows a longer delay between the RA and LA contraction. This can be due to more fluid in the RA and LA and this indicates a worsening of heart failure or the onset of atrial fibrillation (AF). With more fluid build up a stretching of the atrium occurs.

Several embodiments of the present invention include methods that use "far-field" P-waves, similar to surface electrocardiographs (ECG), to determine the electrical activation time of the RA and LA. This could be performed with leadless ECG and EGMs measured from button-type electrodes on the housing of the implantable device. The leadless ECG can, for example, constitute a derived EGM recorded from a button electrode on the housing of the implantable device to a high energy coil-type electrode disposed within a portion of the superior vena cava (SVC). By measuring ambulatory P-wave width, the device can adjust A-V and/or V-V timing to optimize hemodynamics during pacing therapy delivery. The measurement of the P-wave width can be based on a sensed atrial event (A-event) from the bipolar RA EGM. Once a P-wave is sensed, a window around the sensed A-event can be used to detect the P-wave from the far-field EGM. The width can be calculated by first band pass filtering the signal to remove baseline wandering and any noise and determining the P-wave width with an algorithm, such as that used for determining R-wave width in the ICD devices. The present embodiment can be utilized to measure LA electrical activation timing for the purpose of automatically determining an appropriate A-V and/or V-V timing in ambulatory patients with implantable bi-ventricular or CRT devices.

The importance of knowing the width of the signal lies in the fact that it is undesirable to have the LV contract while the LA is still contracting. Synchronous cardiac activity requires complete and complementary contraction of the atrium and the ventricles. Thus, the atrial contribution (including the so-called "atrial kick") to the filling of the LV is maximized. With increased pre-load, the LV contraction is also increased. Therefore, it is desirable to understand, dynamically or on a real-time basis, the relative timing of the RA and, especially the LA. An accurately measured P-wave will provide the width of the RA-to-LA (or vice versa) electrical activation time (herein the "A-A" interval) and once the width (i.e., the duration) is known then an optimized A-V delay can be determined based on that information.

In certain embodiments, the P-wave width is measured either at certain times of the day, and, in other embodiments, the P-wave width is measured on a beat-by-beat basis. This could reduce or eliminate the need for echo-guided A-V and V-V timing optimization at implant or follow-up and provide an on-going optimization in ambulatory patients. Using a far-field EGM is believed to be better than using a near-field EGM in measuring P-wave width, since the far-field EGM approximates a surface ECG measurement.

Certain embodiments of the present invention use an electrode array to obtain a far-field EGM (e.g., a so-called subcutaneous ECG). In these embodiments, an array of electrodes situated on or in proximity to an implanted medical device spaced from a patient's heart couples to logic means and interconnecting circuitry. The logic means (such as a microprocessor) and interconnecting circuitry can selectively detect signals representative of the far-field EGM across selected combinations of the electrodes and the process such signals to record the EGMs in storage for subsequent read-out via telemetry or via a programming device. The logic means can also develop control signals for controlling or modifying the operation of the medical device in accordance with specific attributes of the processed far-field EGM signal.

Although the expression "far-field" is normally employed for sensing from one chamber (or from an electrode not disposed within a chamber) to another chamber of the heart and another electrode (e.g., sensing a P-wave from an ventricular electrode or electrode-pair; sensing an R-wave from an atrial chamber), for purposes of this disclosure, the expression relates not only to this common definition of "far-field", but also to and EGM detected utilizing relatively closely spaced electrodes in the electrode arrays discussed below, wherein the array itself is spaced from the heart. Due to the positioning of the array, the signals may also be referred to as "subcutaneous ECG" signals.

Examples of possible electrode orientations and configurations of a three electrode system comprising electrodes A, B and C are set forth in FIGS. 5A to 5E. In all such systems, it will be understood that the electrodes A, B, C are electrically isolated from one another and the conductive surface of the pulse generator housing 10 through suitable insulating bands and electrical feedthroughs as described in the aforementioned Lindemans U.S. Pat. No. 4,310,000, incorporated herein by reference in relevant part.

FIG. 5A illustrates the orientation of orthogonally disposed electrodes A, B and C with two electrodes on connector block 12 and one electrode on IPG 14. The spacing of the electrodes A, B and C on each of the illustrated orientations of FIGS. 5A to 5E is on the order of about one inch but can be larger or smaller depending on the exact size of the device. Smaller devices and closer spacing will require greater amplification.

The size of implantable pulse generators, particularly single chamber cardiac pacemakers, is growing progressively smaller. FIGS. 5B and 5C illustrate locations of at least one of the electrodes extended away from the pulse generator by a stubby lead extension in FIG. 5B and a segment of the lead itself in FIG. 5C in order to achieve a greater inter-electrode spacing, if desirable.

As illustrated in FIGS. 5C and 5D, the relative orientation of the electrodes may vary somewhat from the orthogonal orientation depicted in FIGS. 5A and 5B. Although orthogonal electrode orientations are often preferred, it will be understood that other angular orientations will suffice and perhaps even be preferred depending on the number of electrodes employed and the signal processing capability of the implanted device.

FIG. 5D depicts the electrodes A, B and C along the sides of the pulse generator 10. It will be understood that the electrodes placed on the edge of the pulse generator case depicted in FIG. 5D could constitute insulated pins of feedthroughs extending through the wall of the case.

Turning again to FIG. 2, an implanted medical device is depicted in order to show the orientation of the array of electrodes A, B, and C in relation to housing 11. An array of three electrodes A, B, and C disposed orthogonally on the surface of IPG 14 and connector block 12 and facing outwardly towards the patient's skin is employed to develop the far-field EGM signal comprising the PQRST signals generated in the sequential depolarization of the atrium and ventricle of the patient's heart.

The far-field EGM reflecting the amplitude and rate of change of the PQRST complex may be sensed throughout the body as an electric field emanating from the electrical depolarization and subsequent repolarization of the heart muscle. As the cardiac muscle depolarizes, the direction of the depolarizing wave front changes. The atria initially depolarize and then the ventricles depolarize down the intraventricular septum to the apex of the heart where the direction of the depolarization changes as the wave front travels back up through the ventricular muscle mass. Consequently, the far-field EGM sensed across the three electrodes A, B, C disposed on the housing will be observed to change both in amplitude and polarity (depending on the orientation of the measuring pair of electrodes in relation to the electric field orientation of the depolarization wave front).

The electrodes A, B and C are fixed in position unless the pulse generator is either moved by the patient or becomes loose in the pocket. In any case, for most applications, it is desirable to optimize the sensing of the peak amplitude of the R-wave for applications relating to simple rate calculation, capture detection or the like by selecting the electrode orientation that provides the highest amplitude R-wave output signal. For other applications, where it is desirable to obtain faithful reproduction of both the amplitude and slew rate of sampled points of the PQRST complex, more elaborate signal processing schemes are described.

Detection of a far-field EGM signal using the RA lead is difficult since the RA lead is highly localized to the right atrium (esp. if either a bi-polar tip-to-ring or a unipolar tip-to-can electrode arrangement is utilized). Thus the RA signal dominates when events are detected using such electrodes coupled to an RA lead thereby essentially precluding the ability to accurately pick up LA contraction signals. Embodiments disclosed herein overcome this obstacle by using a far-field EGM or pseudo ECG to accurately measure the P-waves. Using a pseudo ECG which is the signal at either buttons A, B, or C or from a leadless ECG which incorporates the use of the can, as discussed above, as an alternate to having direct atrial tissue attachment. Thus the signal is seen from afar. Therefore the RA and LA activation is seen and this is very similar to the surface ECG that would represent the RA-LA delay (or less commonly an LA-RA delay). It is of note, that the far field signal is not actually sensing only the LA, but instead is sensing the entire atrial contraction and the timing between the RA and LA electrical conduction (which precedes actual mechanical contraction) is represented by the duration, or width, of the signal. Accordingly, if there is a long A-A delay the P-wave width will be wider, and, if there is a short A-A delay, the P-wave will be narrower.

Obtaining a pseudo ECG or far-field EGM from the housing or canister (sometimes referred to as "can") 11 to SVC electrode 70 or from button electrodes A, B, or C allows IPG 14 to know the width of the RA and LA contraction and essentially the RA to LA delay. The wider the width of the P-wave the longer the delay. Therefore once the P-wave width is known, the A-V timing can be better optimized, either dynamically with IPG 14 or through medication changes possibly with an implantable drug delivery device. This provides increased optimization or on-the-fly kind optimization of A-V timing, which has been shown to improve hemodynamics.

Figure 6:
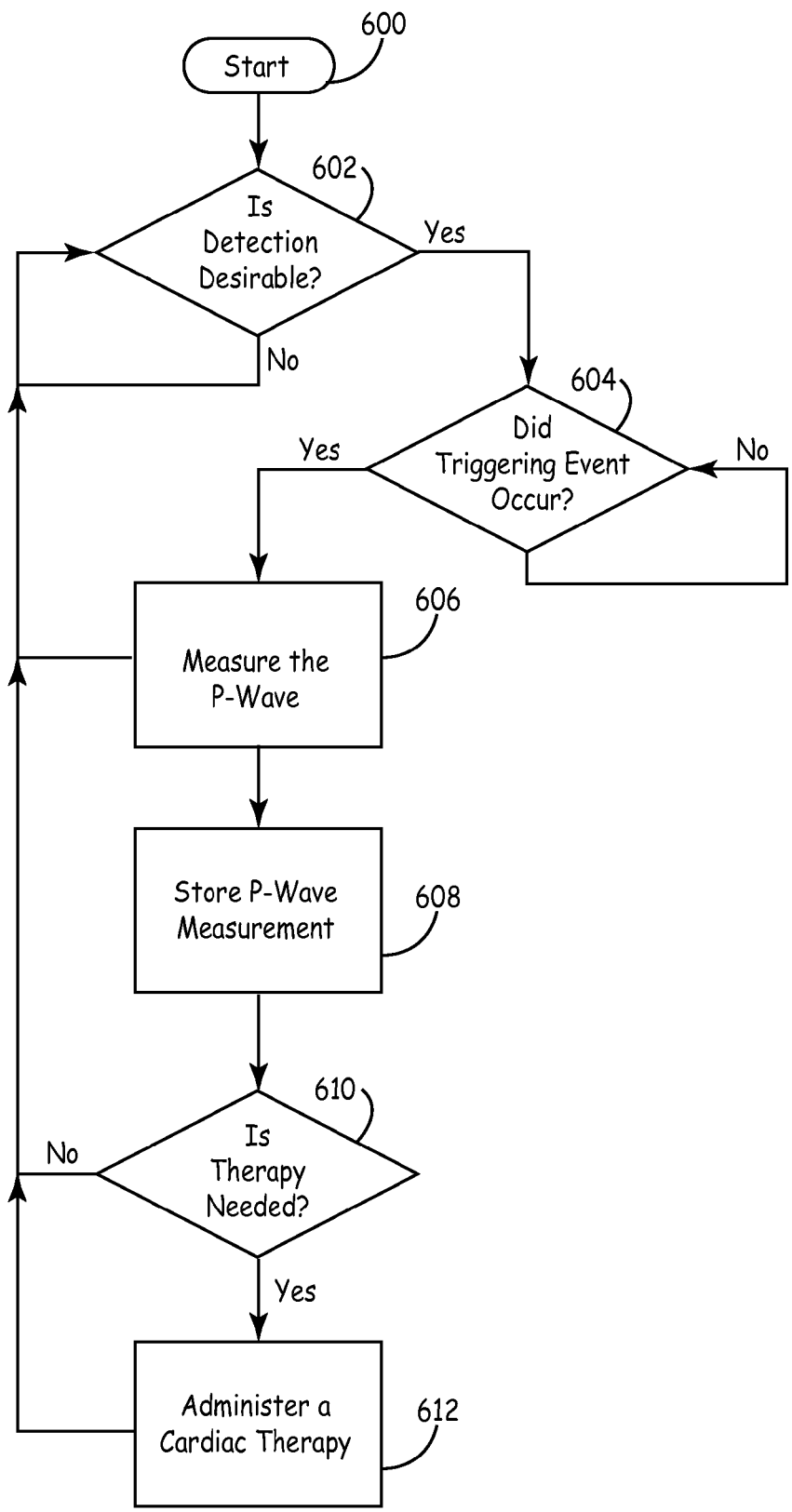
FIG. 6 is a flowchart diagram showing detection of a P-wave in an embodiment of the present invention.

With reference to FIG. 6, a flowchart diagram showing detection of a P-wave width in an embodiment of the present invention is shown. At state 600, microprocessor 102 begins the program. At state 602, microprocessor 102 makes a determination as to whether the time is right to take a P-wave sample. This determination can be based on a variety of variables, such as time of day, activity of the patient, patient position, initiation by patient or physician, either independently or in combination with each variable.

Further, the P-wave measurement does not need to be made constantly. For instance, measurements would be taken at times when the patient is most likely to be asleep. IPG 14 can make this determination using its internal clock. In certain embodiments, the method calls for the use of an activity sensor to know when the patient is stationary and thus taking measurements at that time. Some embodiments include a sensor that detects when the patient is in the supine position. Some embodiments include a patient trigger that allows the patient, clinician or physician to initiate P-wave monitoring if the patient should begin feeling symptomatic. Thus the present invention can reduce certain inconsistencies to better increase the chances of receiving a very clear signal. It may also be desirable to take measurements during both sense and pace events since a true delay may be different during a sense event versus a paced event. This method would provide a close-loop system for A-V and V-V optimization in an ambulatory patient. There is minimal requirement of clinician interaction to set the A-V optimization. Therefore, the A-V timing can be adjusted based on the patient activity, posture, day or night, and changes of heart failure conditions. Therefore the CRT therapy would be optimized at an on-going basis, rather at a point in time after implant.

Referring again to FIG. 6, if microprocessor 102 determines that the time is not good to take a P-wave sample, then the routine returns to state 602. If microprocessor 102 determines that the time is good to take a P-wave sample, then the routine proceeds to state 604 where microprocessor 102 waits for the triggering event. The triggering event can be the RA sense, however, the triggering event can be most anything such as detection of atrial pressure or atrial accelerometer signals without departing from the spirit of the invention. At state 604, microprocessor 102 determines whether the triggering event has occurred. If not, the routine returns to state 604 until the event occurs. If the triggering event occurs, microprocessor 102 then takes a measurement of the P-wave at state 606.

As discussed above, there are challenges in being able to sense the left atrium contraction. It would be desirable to more accurately measure the contraction of the left atrium that could be helpful in adjusting the timing between the left atrium and the left ventricle. Using the RA sense as a trigger in state 604 opens a window for far field detection of the contraction of the left atrium in state 606. This triggering event allows IPG 14 to determine the width of the P-wave. This allows IPG 14 to perform some functions that normally would be performed in a lab, such as optimizing A-V and V-V timing dynamically or in real time. When the P-wave signal is received, in certain embodiments it is run through a band pass filter to reduce the amount of noise on the signal. A good band pass range would be a high-end cutoff at 60 Hz and a low-end cutoff of 30 Hz. The band pass filter also assists in improving the signal to noise ratio.

If obtaining an average P-wave width over several measurements is desired, the routine returns to state 602 to additional P-wave measurements. The P-wave measurement (or multiple measurements) is stored in memory in state 608.

At state 610, microprocessor analyzes all the P-wave information it has accumulated and determines if the P-wave has been widening and determines an average time for electrical activation to propogate between the RA and LA. The P-wave determination can be achieved using algorithms similar to the R-wave width algorithm already implemented in Medtronic single chamber ICDs, or just classic signal processing algorithms such as an "edge" detection algorithm. From this information, microprocessor 102 then makes a determination as to whether cardiac therapy is needed. If not, the routine returns to state 602 and begins the process all over again. If it is determined that a therapy is needed, then the routine proceeds to state 612 where a therapy is administered. This therapy could be an adjustment of the A-V timing so that the time difference between RA and LA is closely related to the time difference between RV and LV. This will assist in increasing the hearts hemodynamics by assuring that the LA has fully contracted before the LV begins contraction. However, it is contemplated that other therapies could be used such as drug delivery from an implantable drug pump without departing from the spirit of the invention. Once the therapy has been administered and set, the program returns to state 602 to begin the process all over again.

To improve the heart's hemodynamics and prevent AF, the present invention suggests using the P-wave width information to dynamically change the A-V delay, either a paced A-V (PAV) or sensed A-V (SAV) delay. IPG 14 could pace the ventricle after the contraction of the left atrium. Thus, the longer the A-A delay a relatively lengthened A-V delay can be programmed or implemented to help restore complementary atrial filling and ventricular ejection of blood (i.e., hemodynamics). This way, the CRT timing can be adjusted automatically based on the changes of P-wave width, as a reflection of the timing of LA contraction. The reverse could also be used. For example, if the patient gets better as reflected in a reduced A-A interval, a therapeutic change of timing for the patient would include shortening the A-V delay to avoid pacing the LV "too late" in the cardiac cycle. Likewise, in the case of CRT delivery an operating V-V interval can be changed to compensate for offset A-A conduction or changing A-A conduction intervals so that ventricular synchrony is maintained or restored.

Once the P-wave width is determined, electrical activation timing of the LA can be determined and the RA electrical activation can be found from the near field P-wave or A sense. At this time, the LA to LV delay can be determined in several ways. 1) from basic physiology, we know the time from electrical activation of atrium to mechanical contraction of the atrium (in the range of 40-60 ms), which is expected to be relatively stable in patients. First, the time from electrical activation of atrium to mechanical contraction of the atrium is known from basic physiology to be in the range of 40-60 ms. This amount is expected to be relatively stable in patients. The A-V timing (in this case RA timing to LV timing) can be determined to be, for instance, the P-wave width plus 60 ms. In addition, for more precise determination, Echo can be used to determine the time of LA electrical activation to atrial contraction (i.e., blood flow into ventricle). This only has to be done once and the number can be entered into the programmer for the device. The RA to RV timing may be determined in a similar way. Therefore the optimized A-V and V-V timing may be achieved.

Thus, embodiments of the CLOSE LOOP OPTIMIZATION OF A-V AND V-V TIMING are disclosed. One skilled in the art will appreciate that the present invention can be practiced with embodiments other than those disclosed. The disclosed embodiments are presented for purposes of illustration and not limitation, and the present invention is limited only by the claims that follow.

The invention claimed is:

1. An implantable medical device, comprising:
a housing including processing means adapted for implantation in a patient;
an implantable lead coupled to the housing;
two or more electrodes mounted on the housing and electrically coupled to the processing means, the two or more electrodes for sensing patient cardiac signals including a far-field EGM, the processing means for determining a width of a P-wave from the sensed far-field EGM; and
a means for delivering a cardiac therapy based upon the width of the P-wave.

2. A device according to claim 1, wherein the two or more electrodes include an electrode operatively coupled to a portion of the housing.

3. A device according to claim 1, wherein the implantable lead comprises an additional electrode.

4. A device according to claim 3, wherein the additional electrode on the implantable lead comprises a high voltage defibrillation electrode.

5. A device according to claim 1, wherein the two or more electrodes include an electrode array.

6. A device according to claim 5, wherein the array of electrodes are disposed orthogonally relative to each other.

7. A device according to claim 1, wherein the two or more electrodes do not contact an atrium of the patient.

8. A device according to claim 7, wherein the means for delivering a cardiac therapy based upon the width of the P-wave, comprises means for adjusting duration of a device-defined A-V interval.

9. A device according to claim 7, wherein the means for delivering a cardiac therapy based upon the width of the P-wave, comprises means for adjusting duration of a device-defined V-V interval.

10. A non-transitory computer-readable medium programmed with instructions for detecting cardiac signals in an implantable medical device, the medium comprising instructions for causing a programmable processor to:
obtaining a far-field EGM signal using sensors of the implantable medical device;
determining a P-wave width from the far-field EGM signal; and
delivering a cardiac therapy based on the determined P-wave width.

11. A medium according to claim 10, further including instructions to determine whether detection by the medical device of a sample cardiac P-wave is desirable.

12. A medium according to claim 11, wherein determining whether detection of the sample cardiac P-wave is desirable is based on at least one of: a time of the day, a posture of a patient, an activity of the patient, an activation by the patient.

13. A medium according to claim 10, further including instructions to determine whether a triggering event occurred.

14. A medium according to claim 13, wherein the triggering event comprises a sensed right atrial contraction.

15. A medium according to claim 13, further including instructions to obtain the far-field EGM signal when a triggering event has occurred.

16. A medium according to claim 10, wherein the cardiac therapy is applied to a left ventricle based on a time difference between a right atrial event and a left atrial event.

17. A non-transitory computer-readable medium programmed with instructions for detecting cardiac signals in an implantable medical device, the medium comprising instructions for causing a programmable processor to:
obtaining a far-field EGM signal using sensors of the implantable medical device;
determining a P-wave width from the far-field EGM signal; and
delivering a cardiac therapy based on the determined P-wave width, including changing an A-V delay interval setting.

18. A non-transitory computer-readable medium programmed with instructions for detecting cardiac signals in an implantable medical device, the medium comprising instructions for causing a programmable processor to:
obtaining a far-field EGM signal using sensors of the implantable medical device;
determining a P-wave width from the far-field EGM signal; and
delivering a cardiac therapy based on the determined P-wave width, including changing a V-V interval setting.

19. An implantable medical device, comprising:
a housing supporting processing means adapted for implantation in a patient;
two or more electrodes electrically coupled to the processing means, the two or more electrodes for sensing patient cardiac signals including a far-field EGM without contacting an atria of the patient, the processing means adapted to determine a width of a P-wave from the sensed far-field EGM; and
a means for adjusting a therapy timing provided by the device based on the determined width of the P-wave.

20. A system according to claim 19, further including a memory for storing multiple P-wave measurements.

21. A system according to claim 19, wherein the therapy timing is adjusted based on the multiple P-wave measurements.

22. A system according to claim 19, wherein the housing supports the two or more electrodes.

23. A system according to claim 19, wherein the therapy timing adjusted comprises duration of a device-defined A-V interval.

24. A system according to claim 19, wherein the therapy timing adjusted comprises duration of a device-defined V-V interval.

\* \* \* \* \*